United States Patent [19]
Schwartz

[11] Patent Number: 4,853,380
[45] Date of Patent: Aug. 1, 1989

[54] COORDINATION COMPLEXES OF PLATINUM USEFUL AS ANTIPROLIFERATIVE AGENTS

[75] Inventor: Paul Schwartz, Rockville, Md.

[73] Assignee: International Pharmaceutical Products, Walnut, Calif.

[21] Appl. No.: 54,883

[22] Filed: May 26, 1987

[51] Int. Cl.[4] .................... A61K 31/555; A61K 31/28
[52] U.S. Cl. .................................... 514/184; 514/492; 556/137
[58] Field of Search ........................ 556/137, 136, 150; 514/184, 492

[56] References Cited

PUBLICATIONS

Translation of USSR Inventor's Certificate 914, 557.

*Primary Examiner*—Paul F. Shaver
*Assistant Examiner*—Stuart L. Hendrickson
*Attorney, Agent, or Firm*—Frank Frisenda, Jr.

[57] ABSTRACT

Platinum complexes are disclosed in which the platinum cation is coordinated to heterocyclic sulfur compounds as well as monodentate or bidentate amines. The complexes have the formula:

$$\begin{array}{c} L_1 \diagdown \quad \overset{R_1}{|}\; S^* - R_2 \\ Pt \qquad\qquad | \\ L_2 \diagup \quad O - S(=O)_2 \end{array}$$

wherein $L_1$ and $L_2$ are individually ammonia or monodentate amine ligands or $L_1$ and $L_2$ together are a bidentate amine ligand, S* is sulfur and $R_1$ and $R_2$ taken together with S are thiophene, thiazole, benzothiazole or benzothiophene. These platinum complexes, which have anti-neoplastic activity, are synthesized by reacting sulfonated heterocyclic sulfur compounds with diamines of platinum nitrate.

32 Claims, No Drawings

COORDINATION COMPLEXES OF PLATINUM USEFUL AS ANTIPROLIFERATIVE AGENTS

BACKGROUND OF THE INVENTION

This invention relates to new platinum complexes in which the platinum cation is coordinated to heterocyclic sulfur compounds as well as monofunctional or bidentate amines. It relates also to a method for using these complexes to treat neoplastic disease in mammals.

Platinum complexes have been known to inhibit cell division by antimitotic activity since 1965, (Rosenberg et al., Nature 205, 698 (1965)). Since that time many such complexes have been prepared and tested for anticancer activity in animal tumor screening systems, and one of the most effective complexes, cis-dichlorodiammine platinum (II) (cis-Platin) is used clinically for treatment of certain human tumors.

However, cis-Platin as well as other complexes of its type have toxic side effects which limit the therapeutic, dose. Morbidity in human patients include hematological, renal and neural (8th nerve) damage. See, e.g., Leh and Wolfe, J. Pharmaceut. Sci. 65, 315–328 (1976). For this reason there has been an effort to synthesize platinum complexes that are more active against tumor cells while having less toxicity.

The effects of substituents in platinum complexes are not well understood. Most complexes synthesized for testing in animal tumor systems have not differed substantially from the cis-Platin model. Such complexes are typically of the form:

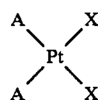

wherein A is a carrier ligand, typically a monodentate or bidentate amine and X is a leaving group, typically a chloride ion. The carrier ligand A is believed to promote the activity of the complex by facilitating its transport into the cell by means, for example, of favorable stearic factors, hydrophilic or lipophilic character or structural and electronic properties that promote binding to cell receptors.

The leaving groups are believed play a more direct role and their effectiveness is linked to the ease with which hydrolysis of the platinum-X bond can occur. Complexes of ligands that hydrolyze rapidly, such as $NO_3$- are highly toxic. Those that hydrolyze slowly, such as $CN^-$, are generally inactive.

The most active complexes have halide or carboxylic leaving groups [Hydes, in Platinum Coordination Complexes in Cancer Chemotherapy, Hacker et al., (eds.) M. Nijhoff Publishing (1984)]. Novel complexes involving sulfur leaving groups have been infrequently investigated and these have usually been mondentate groups [Foye and Kaewchanslip, J. Pharmaceut. Sci. 68(9), 1131–1135 (1979)]; U.S. Pat. No. 4,578,491 (Amundsen, et al., 1986).

The present invention is directed to a new class of platinum complexes in which the platinum is coordinated to a bidentate heterocyclic sulfur-containing group. It is believed that these sulfur bonded complexes have a different spectrum of activity than the conventional cis-Platin analogues, and will offer clinical alternatives to cis-Platin chemotherapy. It is an object of the invention to provide a method for synthesizing heterocyclic sulfur complexes of platinum. Another object is to provide a method to use these complexes in the treatment of neoplastic disease in mammals.

BRIEF DESCRIPTION OF THE INVENTION

In accordance with one aspect of the present invention, there is provided a compound having the formula:

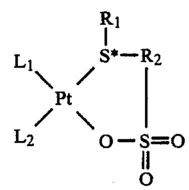

FORMULA 1 wherein $L_1$ and $L_2$ are individually ammonia or monodentate amine ligands or $L_1$ and $L_2$ together comprise a bidentate amine ligand; S* is sulfur; and $R_1$ and $R_2$ together with S* comprise a monocyclic and bicyclic sulfur-containing heterocycles. The heterocyclic moiety is preferably aromatic, and may advantageously be selected from the group consisting of thiophene, thiazole, benzothiazole, and benzothiophene, substituted or unsubstituted.

Alternatively, in another embodiment, $L_1$ and $L_2$ are individually ammonia or are amines selected from the group consisting of branched or straight chain lower (C1–C10) alkyl and alkenyl amines, hydroxylated and polyhydroxylated amines, aryl amines, aralkylamines, saturated and unsaturated cyclic and polycyclic hydrocarbon amines, amines of cyclic nitrogen compounds, and triazines.

In still another embodiment, $L_1$ and $L_2$ together comprise a bidentate amine ligand selected from the group consisting of branched or straight chain lower (C1–C10) alkyl and alkenyl diamines, hydroxylated and polyhydroxylated diamines, aryl diamines, aralkyl diamines, saturated and unsaturated cyclic and polycyclic hydrocarbon diamines, amines of cyclic nitrogen compounds, and triazines. A preferred cyclic hydrocarbon ligand is diaminocyclohexane.

In one preferred embodiment, the compound has the formula:

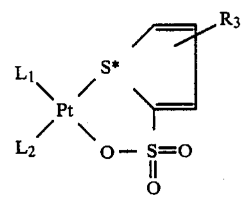

FORMULA 2 wherein $R_3$ is selected from the group consisting of hydrogen, halogen, hydroxy, nitro, and substituted or unsubstituted lower ($C_1$–$C_4$) alkyl, alkoxy, or alkylene.

In another preferred embodiment, the compound has the formula:

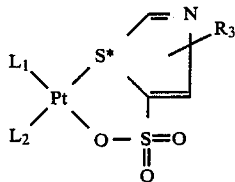

wherein $R_3$ is selected from the group consisting of hydrogen, halogen, hydroxy, nitro, and substituted or unsubstituted lower ($C_1$–$C_4$) alkyl, alkoxy, or alkylene.

In still another preferred embodiment, the compound has the formula:

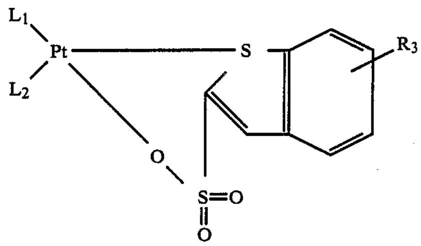

wherein $R_3$ is selected from the group consisting of hydrogen, halogen, hydroxy, nitro, and substituted or unsubstituted lower ($C_1$–$C_4$) alkyl, alkoxy or alkylene.

Some of the specifically preferred compounds include 2-thiophene sulfonato (trans-1,2-diaminocyclohexane)platinum; 2-methyl-5-thiophene sulfonato (trans-1,2-diaminocyclohexane) platinum; 2-bromo-5-thiophene sulfonato (trans-1,2-diaminocyclohexane) platinum; 2-chloro-5-thiophene sulfonato (trans-1,2-diaminocyclohexane)platinum; 2-thiazole sulfonato (trans-1,2-diaminocyclohexane) platinum; 2-methyl-5-thiazole sulfonato (trans-1,2-diaminocyclohexane) platinum; 2-bromo-5-thiazole sulfonato (trans-1,2-diaminocyclohexane) platinum; 6-chloro-2-thiazole sulfonato (trans-1,2-diaminocyclohexane) platinum; 2-benzothiophene sulfonato (trans-1,2-diaminocyclohexane) platinum; 6-methyl-2-benzothiophene sulfonato (trans-1,2-diaminocyclohexane) platinum; 6-bromo-2-benzothiophene sulfonato (trans-1,2-diaminocyclohexane) platinum; and 6-chloro-2-benzothiophene sulfonato (trans-1,2-diaminocyclohexane) platinum.

In another embodiment of the present invention, there is provided a compound having the formula:

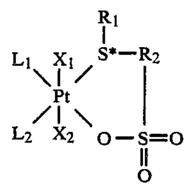

wherein $L_1$ and $L_2$ are individually ammonia or monodentate amine ligands or $L_1$ and $L_2$ together comprise a bidentate amine ligand; $X_1$ and $X_2$ are two like groups selected from hydroxyl and halogen, such as chloride or bromide; S* is sulfur; and $R_1$ and $R_2$ together with S* comprise a heterocyclic moiety selected from the group consisting of thiophene, thiazole, benzothiazole, and benzothiophene, substituted or unsubstituted.

Preferred bidentate ligands include cyclic hydrocarbon ligands, such as diaminocyclohexane. The sulfur-containing ligands and the amine ligands may advantageously be the same as those used on the platinum (II) complexes described above.

In accordance with another aspect of the present invention, there is provided a method for preparing a coordination complex of platinum comprising the steps of reacting a platinum salt with monofunctional or difunctional amine at a molar ratio of amine functionality to platinum of about 2:1 to yield a platinum-diamine complex; obtaining a heterocyclic sulfur compound wherein a ring carbon atom adjacent to the heterocyclic sulfur atom has a pendant sulfonic acid moiety bonded thereto; and reacting the heterocyclic sulfur compound with the platinum amine complex to yield a product in which platinum is coordinated to two amine moieties, the heterocyclic sulfur atom, and the sulfonic acid moiety.

The method may optimally further comprise the step of reacting the product with an oxidizing agent to yield a compound in which platinum has an oxidation state of +4 and is further coordinated to two hydroxyl or halide groups. Preferred oxidizing agents include hydrogen peroxide, halogen, and halogen acids.

The reaction temperatures may be any temperature at which the reactions will occur, such as from about 4° C. to about 35° C. The reactions are carried out for a suitable length of time, such as from about 4 to about 80 hours, preferably for about 8 to about 24 hours, or until formation of the product of each reaction is substantially complete.

In one preferred embodiment, the heterocyclic sulfur compound is substituted or unsubstituted thiophene, thiazole, benzothiophene or benzothiazole.

In accordance with yet another aspect of this invention, any of the compounds disclosed above may be used in a method for inhibiting the growth of neoplastic cells by administering to a mammal with neoplastic disease a therapeutically effective dose of one of those compounds.

In accordance with yet another aspect of the present invention, there is provided a pharmaceutical preparation, comprising one of the compounds disclosed above in combination with a pharmaceutically-acceptable carrier.

DETAILED DESCRIPTION OF THE INVENTION

The present invention provides a novel class of platinum complexes in which the two leaving groups are part of a single heterocyclic moiety. One of the leaving groups is a sulfonic acid moiety; the other is a heterocycle which is bonded to the platinum through a heterocyclic sulfur. The sulfonic acid leaving group is covalently bound to the sulfur-containing heterocycle. It is believed that this novel chemistry provides, on a single platinum, both a rapidly-hydrolyzing sulfonic acid leaving group and a slowly-hydrolyzing sulfur-containing heterocycle, to which the sulfonic acid group is attached. It is further believed that, upon hydrolysis of the sulfonic acid-platinum bond, an active platinum is produced which can interact with the genetric material of a rapidly-growing cell in a manner that will disrupt the genetic machinery and result in cell death.

In the compounds of the present invention, the platinum atom may be either in the +2 or the +4 oxidation state. Formula 1 (above) represents platinum in the +2 oxidation state. Formula 5 (above) represents platinum in the +4 oxidation state. In either case, the molecule is provided with amine carrier ligands $L_1$ and $L_2$ and a bidentate ligand of the formula:

FORMULA 6

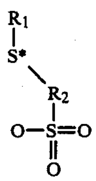

wherein $R_1$ and $R_2$ together with S* comprise a monocyclic or bicyclic sulfur-containing heterocycle. The heterocyclic moiety is preferably an aromatic heterocycle, and may advantageoysly be selected from thiophene, thiazole, benzothiazole and benzothiophene. However, other sulfur-containing heterocycles may also be used. The heterocyclic moiety may be unsubstituted, or may be substituted at any open site with halogen, hydroxy, nitro, and substituted or unsubstituted lower ($C_1$–$C_4$) alkyl, alkoxy, alkylene. Such substituents include methyl, ethyl, propyl, isopropyl, n-butyl, isobutyl, t-butyl, chloromethyl, chlorofluoromethyl, trichloromethyl, trifluoromethyl, dichloroethyl, hydroxymethyl, hydroxyethyl, hydroxypropyl, methoxy, ethoxy, chloromethoxy, propylene, isobutylene and similar substituted or unsubstituted groups. The substituent $R_3$ may be located at any available position on the heterocycle; however, in one preferred embodiment, it is located on a carbon adjacent to the heterocyclic sulfur atom.

The carrier ligands $L_1$ and $L_2$ are not believed to be particularly critical to the present invention and may be any amine ligands that are suitable for use in antitumor platinum complexes. A large number of such ligands are known. The class of suitable ligands includes monodentate ligands, such s ammonia, branched or straight chain lower ($C_1$–$C_{10}$) alkyl and alkenyl amines, hydroxylated and polyhydroxylated amines, aryl amines, aralkyl amines, saturated and unsaturated cyclic and polycyclic hydrocarbon amines, amines of heterocyclic nitrogen compounds, and triazines. Specific monodentate ligands may include methyl, ethyl, n-propyl, isopropyl, n-butyl, n-octyl or isooctyl amines, 2-methyl-2-amino-1-propanol, 2,3-dihydroxypropylamine, aniline, o-ethylaniline, phenethylamine, nitroaniline (o, m or para), methoxyaniline (o, m or para), naphthylamine (1 or 2), benzylamine, 2-naphthyl-1-ethylamine, cyclopropyl through cycloheptyl amines, 2-cyclopenten-1-yl and 2-cyclohexen-1-yl amines, 1-adamantanamine, endo or exo bornaneamine, pyrrole, ethylenimine, azepine, indole, carbazole, pyridine, pyrazine, pyrimidine, acridine, quinoline and isoquinoline. Similarly, suitable bidentate amine ligands may be selected from the group consisting of branched or straight chain lower ($C_1$–$C_{10}$) alkyl and alkenyl diamines, aryl diamines, hydroxylated and polyhydroxylated amines, aralkyl diamines, saturated and unsaturated cyclic and polycyclic hydrocarbon diamines, amines of heterocyclic nitrogen compounds, and triazines. Specific bidentate ligands may include 1,2-diaminoethane, 1,3-diaminopropane, 1,4-diaminobutane, o-phenylene diamine, 4,5-dimethyl-o-phenylenediamine, ethylene diamine, dimethylethylenediamine, 1,1-diaminomethylcyclohexane, 1-amino-2-aminomethylcyclohexane, 1,8-diaminonaphthalene, 2- and 3-aminomethylpiperidine, 2,4-diaminopyridine, diaminoacetone, 1,3-diamino-2-propanol, 2,3-bis(hydroxymethyl) ethylene diamine, 1,2-diamino-4,5-dihydroxycyclohexane. One particularly preferred diamine is diaminocyclohexane.

In the platinum (IV) compounds of Formula 6, in addition to $L_1$, $L_2$, $R_1$ and $R_2$, the substituents $X_1$ and $X_2$ are present to fill the additional valences on the platinum atom. $X_1$ and $X_2$ are preferably the same, and are preferably either hydroxyl or halogen, such as chloride or bromide.

The compounds of the present invention may be administered to mammals suffering from neoplastic disease to slow the growth of neoplastic cells and prolong the life expectancy of the mammal. Indications for which the various compounds of the present invention are believed to be useful include bronchial, testicular, ovarian, cervical, prostate, endometrial and bladder neoplasms, as well as neoplastic disease of the bone marrow or of the blood cells.

In general, an effective dose of a compound according to the present invention will be administered to a mammal suffering from neoplastic disease from one to four times per day. An effective dosage, calculated in relation to the body weight of the mammal, will generally be between about 1 and about 500 mg/kg, more preferably between about 2 and about 100 mg/kg, and most preferably between about 3 and about 50 mg/kg. In many instances, it is believed that a dosage of about 10–30 mg/kg administered from about one to three times will produce good results. Of course, in the treatment of humans, the exact dosage will be determined in each instance by the treating physician, taking into account the condition of the patient, the stage of tumor development, and other treatments the patient may be receiving or may have received. In general, as a starting point, treatment regimens similar to those used with cis-Platin may be used with the compounds of the present ivention. The compound may be administered orally or parenterally. The term parenteral is used herein includes subcutaneous injection, intravenous, intramuscular or intrasternal injection, or infusion techniques.

In one preferred embodiment of the present invention, the compounds of the present invention are formulated into pharmaceutical preparations. These pharmaceutical preparations include one or more of the compounds of the present invention, and may further include other pharmaceutically effective active ingredients. In addition, any of the well-known pharmaceutically-acceptable carriers or excipients may be combined with the compounds of the present invention in a well-known manner. The pharmaceutical compositions may be provided in individual dosage units. Each unit may contain a pharmaceutically effective amount of active ingredient. For use in humans, one embodiment of the present invention may provide individual dosage units containing between about 100 mg and about 2,000 mg of the active molecule. The pharmaceutical composition may be in any form suitable for oral use, such as tablets, suspensions, dispersible powers, emulsions, capsules or elixirs. Coloring, flavoring, sweetening and preserving agents may also be provided.

Tablets or capsules may be provided containing the active ingredient or ingredients in admixture with non-toxic pharmaceutically acceptable excipients. Suitable excipients, include inert diluents, such as calcium carbonate, sodium carbonate, lactose, calcium phosphate; binding agents, such as starch, gelatin, or acacia; or lubricating agents, such as magnesium stearate, stearic acid or talc. Moreover, oral compositions may be coated by known techniques to delay disintegration and absorption in the gastrointestinal tract, thereby providing sustained action.

Aqueous suspensions, containing conventional suspending agents, dispersing or wetting agents, preservatives, coloring agents, flavoring agents and sweetening agents may be formulated in accordance with industry standards. Similarly, dispersible powders and granules for preparation of aqueous suspensions by the addition of water may be provided.

The compositions of this invention may be provided in individual dosage form to be administered parenterally. Parenteral compositions may be made by formulating the compounds of the present invention into injectable aqueous or oily solutions or suspensions, in a manner that is well known.

Injectable carriers can be solvent or dispersion media containing, for example, water, ethanol, glycerol, propylene glycol, polyethylene glycol and vegetable oils. The injectable solutions may include conventional antibacterial or antifungal agents, such as parabens, chlorobutanol, phenol, sorbic acid, thimerosal, and the like. In addition, buffers may be used to maintain the composition at physiological pH or at a slightly lower pH (e.g., 5 or 6). The solutions may be made isotonic by the addition of conventional materials such as sodium chloride and/or sugars.

The invention contemplates the use of the compound of claim 1 in the manufacture of medicaments for the treatment of various malignant diseases including bronchial, testicular, ovarian, cervical, prostatic, endometrial and bladder neoplasms as well as neoplastic disease of the bone marrow or blood cells, by combining the compound of claim 1 with a pharmaceutically acceptable carrier, excipient or solvent in preparations wherein the compound is present in proportions of about one part per hundred to about 99 parts per hundred.

The compound of claim 1 may be used in the manufacture of solutions for injection. For example, 9 grams of sodium chloride may be dissolved with stirring in 800 ml of water suitable for injection purposes and the pH adjusted to 2.5–3.5 (preferably 3.0) with concentrated hydrochloric acid (38%). Then with stirring there is dissolved 1 gram of a compound of claim 1. The pH is controlled and if necessary, it is again adjusted to 2.5–3.5 with hydrochloric acid. Finally, the volume is brought up to 1 liter with water suitable for injection purposes and the pH was again checked.

This solution is sterile filtered under aseptic conditions by means of a membrane filter having a pore diameter of 0.22 um and filled to 50 ml in 50 ml injection flasks (brown) of hydrolytic class I. The injection flasks are closed with Teflon-coated rubber stoppers and provided with aluminum flanged lids. One ml of solution contains 1 mg of active material.

The compound of claim 1 may also be used in the manufacture of a lyophilizate which may be reconstituted for intravenous use. For example, 9 grams of sodium chloride and 10 grams of mannitol may be dissolved with stirring in 800 ml of water suitable for injection purposes. The pH is adjusted with concentrated hydrochloric acid (38%) to a pH of 2.5–3.5 (preferably 3.0). There is dissolved in this solution with stirring 1 gram of the compound of claim 1. The pH is controlled and if necessary adjusted again with hydrochloric acid to 2.5–3.5 Finally the volume is brought up to 1 liter with water suitable for injection purposes and the pH checked again.

This solution is sterile-filtered under aseptic conditions by means of a membrane filter having a pore diameter of 0.22 um and filtered to 10 ml in brown 15 ml injection flasks of hydrolytic class I. These flasks are provided with a freeze-drying stopper and lyophilized in a suitable apparatus. After drying, the flasks are gassed with sterile, dry, nitrogen and the flasks finally closed in the apparatus. The stoppers are secured by a border lid.

For intravenous use the lyophilizate is reconstituted in 10 ml of water suitable for injection purposes.

One ml of solution contains 1 mg of active material.

The complexes of this invention may be prepared by the general method outlined below.

General Synthetic Method

The complexes of the invention are prepared by the reaction of sulfonated heterocyclic sulfur compounds with diamines of platinum nitrate.

Heterocyclic sulfur compounds are sulfonated according to a modification of a procedure described by Shustareve and Passet in U.S.S.R. Pat. No. 2,967,477 (Mar. 25, 1982), and using a dimethylformamide sulfur complex, DMF-$SO_3$, prepared by the method of Garbrecht, J. Org. Chem. 24, 368 (1959).

The reaction of liquefied sulfonic acid with dimethylformamide yields the DMF-$SO_3$ complex. Reaction of DMF-$SO_3$ with a selected sulfur heterocycle yields the corresponding sulfonated compound, Formula 7.

FORMULA 7

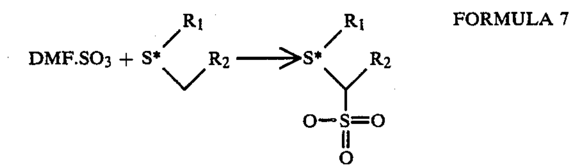

The platinum reagent is prepared by a standard procedure. Dipotassium platinum chloride reacts with amines of diamines to form the dichloro (diamino) platinum complex. Further reaction with $AgNO_3$ yields the dinitrato (diamino) platinum complex. (Formula 8).

FORMULA 8

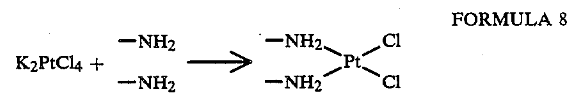

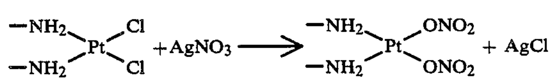

Reaction of dinitrato (diamino) platinum (Formula 8) with sulfonated sulfur heterocycles (Formula 7) yields the desired corresponding heterocycle sulfonate diamine platinum complex, Formula 1.

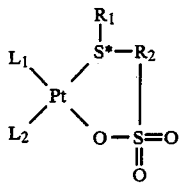

FORMULA 1

Details of this synthesis, together with modifications and variations specifically tailored for particular compounds, are set out more fully in the specific examples which follow.

Examples 1 through 4 illustrate the synthesis of complexes of this invention, where $R_1$ and $R_2$, together with the heterocyclic sulfur atom to which they are attached, comprise a thiophene structure. The remaining synthetic Examples illustrate synthesis of other related complexes.

EXAMPLE 1

2-bromo-5-thiophene sulfonato (trans-1,2-diaminocyclohexane) platinum (II)

A. Preparation of sulfonating agent

Liquefied sulfur trioxide, $SO_3$ (250 g) was added to 2.5 liters of dry dimethylformamide, DMF, with stirring at 0° C. The $SO_3$ was added over a period of 4 hours at a rate slow enough to maintain the temperature below 5° C. After the addition of DMF, the solution was stirred at 5° C. for an additional two hours. The resulting yellow DMF-$SO_3$ solution was stored at 4° C.

B. Preparation of 2-bromo-5-sulfothiophene

Commerically-available 2-bromothiophene (6.65 gm; 40 mmol) was placed in 200 ml of dichloroethylene and an equimolar amount of the DMF-$SO_3$ complex added. The mixture was heated to 50° C. for 3 hours and then left at room temperature overnight. It was then poured into 150 ml of water. The product was extracted into the water layer and $Ba(OH)_2.8H_2O$ was added until neutral pH was obtained. The insoluble barium sulfate was filtered off and the filtrate was dried by evaporation to near dryness. Ethanol and ether were added to precipitate 2.4 gms (20%) of barium 2-bromo-5-thiophene sulfonate. This barium salt was dissolved in water and an equivalent amount of sodium carbonate was added. Barium carbonate precipitated immediately. The filtrate was evaporated and ethanol and ether were added to precipitate sodium 2-bromo-5-thiophene sulfonate in 88% yield.

Proton nmr: 7.3 ppm (doublet); 7.15 ppm (doublet).

Thin-layer chromatography: reverse phase on silica using acetonitrile/$H_2O$ (9/1) gave one spot with $R_f$=0.69.

C. Preparation of dichloro (trans-1,2-diaminocyclohexane) platinum

Potassium tetrachloroplatinate (23.5 gm; 0.056 mol) was dissolved in 250 ml of deionized water. An equimolar quantity of (trans-1,2-diaminocyclohexane) (6.4 gm; 0.056 mol) was dissolved in 10 ml of water and the pH was adjusted to 7.5 using 6N HCl. The amine solution was added to the red $K_2PtCl_4$ solution and the pH was adjusted to 9 with 5N KOH. A yellow precipitate formed. The mixture was stirred overnight and the yellow product was then filtered off, washed with water and dried in a vacuum desiccator for two days to yield 20.7 gm (96% yield) of dichloro (trans-1,2-diaminocyclohexane) platinum.

D. Formation of (trans-1,2-diaminocyclohexane) platinum nitrate

Dichloro (trans-1,2-diaminocyclohexane) platinum (1.0 g; 2.6 mmol) and 0.85 g of silver nitrate (5.0 mmol) were added to 25 ml of $H_2O$ and the mixture was stirred in a flask protected from light at room temperature overnight. The insoluble silver chloride was filtered off on a fine sintered glass funnel and the product, dinitrato (trans-1,2-diaminocyclohexane) platinum, remained in the filtrate.

E. Formation of the platinum complex

The filtrate of "D," above was combined with an aqueous solution of sodium 2-bromo-5-thiophene-sulfonate (0.75 g; 2.6 mmol). The pH of the reaction mixture was adjusted to 5 to precipitate out theproduct. The precipitate was washed with water and ethanol and dried in vacuo to yield 0.98 g (68%) of 2-bromo-5-thiophene sulfonato (trans-1,2-diaminocyclohexane) platinum (II).

Elemental analysis of the dried product gave: C: 21.53; H: 2.87; N: 4.99; S: 11.64; Br: 13.92; Pt: 35.59.

Calculated values for $C_{10}H_{16}N_2S_2O_3BrPt.2H_2O$ are: C: 21.78; H: 2.92; N: 5.08; S: 11.63; Br: 14.49; Pt: 35.38.

EXAMPLE 2

2-chloro-5-thiophene sulfonato (trans-1,2-diaminocyclohexane) platinum (II)

The procedure of Example 1 was followed using 2-chlorothiophene (4.8 g; 40 mmol) in lieu of the 2-bromothiophene used therein. The synthesis yielded 3.5 g (33%) of the barium salt. The barium salt was converted to the sodium salt according to the procedure of Example 1B. Sodium 2-chloro-5-thiophene sulfonate precipitated for ethanol/ether in 88% yield.

Thin layer chromatography: Reverse phase on silica using acetonitrile/$H_2O$ (9/1) gave one spot with $R_f$=0.9.

The platinum complex was prepared by reacting (trans-1,2-diaminocyclohexane dinitrate prepared as in Example 1D with sodium 2-chloro-5-thiophene sulfonate (0.37 g; 1.72 mmol) in aqueous solution. The product was precipitated, washed and dried as described in Example 1D to yield 0.33 g (38%) of 2-chloro-5-thiophene sulfanato (trans-1,2-diaminocyclohexane) platinum (II).

Elemental analysis of the dried product gave: C: 21.90; H: 3.45; N: 5.23; S: 10.49; Cl: 6.88; Pt: 36.46.

Calculated values for $C_{10}H_{16}N_2ClS_2O_3Pt.2H_2O$ are: C: 22.11; H: 3.68; N: 5.15; S: 11.80; Cl: 6.53; Pt: 35.95.

EXAMPLE 3

2-methyl-5-thiophene sulfonato (trans-1,2-diaminocyclohexane) platinum (II)

The procedure of Example 1 was followed using 2-methylthiophene in lieu of the 2-bromothiophene used therein.

In the sulfonation step, Example 1B, 2-methylthiophene (8 g; 0.08 mol) was added to 200 ml of dichloroethylene. An equimolar amount of the DMF-$SO_3$ complex was then added and the mixture was kept at room temperature for 3 hours and then poured into 150 ml of water. The product was extracted into the water layer and $Ba(OH)_2.8H_2O$ was added until neutral pH(7) was obtained. The insoluble barium sulfate was filtered off and the filtrate was evaporated to near dryness. Ethanol and ether was added to precipitate 7 grams (40%) of barium 2-methyl-5-thiophene sulfonate. This barium salt was dissolved in water and an equivalent amount of sodium carbonate was added. Barium carbonate precipitated immediately. The filtrate was evaporated and ethanol and ether were added to precipitate sodium 2-methyl-5-thiophene sulfonate in 90% yield.

Proton nmr: 7.25 ppm (doublet); 6.8 ppm (multiplet); 2.5 ppm (singlet).

Thin-layer chromatography: reversed phase on silica using acetonitrile/$H_2O$ (9/1) gave one spot with $R_f=0.59$.

This sulfonate was used in place of the sodium 2-bromo-5-thiophene sulfonate in the procedure used in Example 1. The synthesis yielded 1.3 g of 2-methyl-5-thiophene sulfonato (trans-1,2-diaminocyclohexane) platinum (II). Yield 38%.

Elemental analysis of the dried product gave: C: 25.99; H: 3.89; N: 6.00; S: 11.93; Pt: 40.10

Calculated for $C_{11}H_{19}N_2S_2O_3Pt.H_2O$: C: 26.19; H: 4.16; N: 5.56; S: 12.19; Pt: 38.71.

EXAMPLE 4

2-thiophene sulfonato (trans-1,2-diaminocyclohexane) platinum (II)

The procedure of Example 1 was repeated using unsubstituted sodium 2-thiophene sulfonate (1.0 gm; 4.9 mmol) and dinitrato (trans-1,2-diaminocyclohexane) platinum (2.12 g; 4.9 mmol). The synthesis yielded 0.5 g (21%) of 2-thiophene sulfonato (trans-1,2-diaminocyclohexane) platinum (II).

Elemental analysis of the dried product gave: C: 23.72; H: 3.59; N: 5.52; S: 12.37; Pt: 39.35.

Calculated for $C_{10}H_{17}N_2S_2O_3Pt.2H_2O$: C: 23.62; H: 3.93; N: 5.51; S: 12.59; Pt: 38.38.

EXAMPLE 5

2-bromo-5-thiazole sulfonato (trans-1,2-diaminocyclohexane) platinum (II)

The procedure of Example 1 is followed using 2-bromothiazole in lieu of the 2-bromothiophene therein described.

EXAMPLE 6

6-bromo-2-benzothiophene sulfonato (trans-1,2-diaminocyclohexane) platinum (II)

The procedure of Example 1 is followed using 6-bromobenzothiophene in lieu of 2-bromothiophene.

EXAMPLE 7

2-bromo-5-thiophene sulfonato (trans-1,2-diaminocyclohexane) dihydroxy platinum (IV)

The product of Example 1 is further oxidized to the +4 oxidation state by reaction of the complex with hydrogen peroxide.

EXAMPLE 8

Examples 1-6 are repeated, except that the trans-1,2-diaminocyclohexane (platinum) nitrate of those Examples is replaced with an equimolar amount of bis(2-aminopropane) platinum nitrate (prepared by reaction of 2-aminopropane with $K_2PtCl_4$, and reaction of the resulting compound with $AgNO_3$) to make the corresponding bis(2-aminopropane) platinum complex.

EXAMPLE 9

Antitumor Properties of the Complexes

The complexes were tested for antitumor properties using the L1210 murine leukemia test line.

In a typical experiment, 1,000,000 tumor cells were injected into $BDF_1$ mice intraperitoneally. One day 1, after the cell inoculum, one group of the mice were treated by intraperitoneal injection of 1% sodium bicarbonate solutions of the complexes. The %T/C value is calculated by comparing the mean survival time of treated animals to that of the control (untreated) animals.

Activity is indicated if treated mice (T) have an increased life span compared to untreated (control) mice (C) of at least 40% (T/C 140%).

TABLE 1

L1210: Activity of 2-substituted thiophene sulfonic acid platinum complexes:

| Substituent | Dose (mg/kg) | % T/C |
|---|---|---|
| H | 5 | 151 |
| | 10 | 176 |
| | 20 | 160 |
| $CH_3$ | 5 | 163 |
| | 10 | 227 |
| Br | 5 | 147 |
| | 10 | 181 |
| Cl | 10 | 250 |

What is claimed is:

1. A compound having the formula:

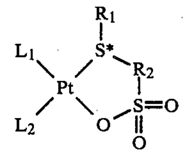

wherein $L_1$ and $L_2$ are individually ammonia or monodentate amine ligands or $L_1$ and $L_2$ together comprise a bidentate amine ligand;

S* is sulfur; and $R_1$ and $R_2$ together with S* comprise a heterocyclic moiety selected from the group consisting of thiophene, thiazole, benzothiazole and benzothiophene, substituted or unsubstituted.

2. A compound according to claim 1, wherein $L_1$ and $L_2$ together comprise a didentate amine ligand.

3. A compound according to claim 1, wherein said bidentate ligand is a cyclic hydrocarbon ligand.

4. A compound according to claim 3, wherein said ligand is 1,2 diaminocyclohexane.

5. A compound according to claim 1, wherein $L_1$ and $L_2$ are individually ammonia or are amines selected from the group consisting of branched or straight chain lower (C1-C10) alkyl and alkenyl amines, aryl amines, aralkylamines, saturated hydrocarbon amine, unsaturated cyclic hydrocarbon amine, and polycyclic hydrocarbon amine, and triazines.

6. A compound according to claim 1, wherein $L_1$ and $L_2$ together comprise a bidentate amine ligand selected from the group consisting of branched or straight chain lower (C1-C10) alkyl and alkenyl diamines, aryl diamines, aralkyl diamines, and wherein the group $R_3$ is bound to one carbon atom, separate and distinct from both rings.

7. A compound according to claim claim 1, 2, 3 or 4, having the formula

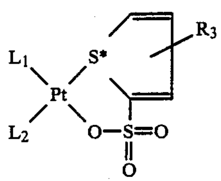

wherein $R_3$ is selected from the group consisting of hydrogen, halogen, hydroxy, nitro and substituted or unsubstituted lower ($C_1$–$C_4$) alkyl, alkoxy or alkylene.

8. A compound according to claim 1, 2, 3, or 4, having the formula

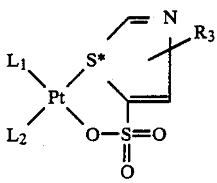

wherein $R_3$ is selected from the group consisting of hydrogen, halogen, hydroxy, nitro and substituted or unsubstituted lower ($C_1$–$C_4$) alkyl, alkoxy or alkylene and wherein the group $R_3$ is bound to one carbon atom, separate and distinct from both rings.

9. A compound according to claim 1, 2, 3 or 4, having the formula

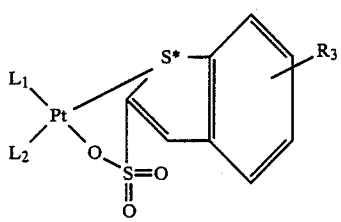

wherein $R_3$ is selected from the group consisting of hydrogen, halogen, hydroxy, nitro and substituted or unsubstituted lower ($C_1$–$C_4$) alkyl, alkoxy or alkylene and wherein the group $R_3$ is bound to one carbon atom, separate and distinct from both rings.

10. A compound according to claim 1, which is 2-thiophene sulfonato (trans-1,2-diaminocyclohexane) platinum.

11. A compound according to claim 1, which is 2-methyl-5-thiophene sulfonato (trans-1,2-diaminocyclohexane).platinum.

12. A compound according to claim 1, which is 2-bromo-5-thiophene sulfonato (trans-1,2-diaminocyclohexane) platinum.

13. A compound according to claim 1, which is 2-chloro-5-thiophene sulfonato (trans-1,2-diaminocyclohexane) platinum.

14. A compound according to claim 1, which is 2-thiazole sulfonato (trans-1,2-diaminocyclohexane) platinum.

15. A compound according to claim 1, which is 2-methyl-5-thiazole sulfonato (trans-1,2-diaminocyclohexane) platinum.

16. A compound according to claim 1, which is 2-bromo-5-thiazole sulfonato (trans-1,2-diaminocyclohexane) platinum.

17. A compound according to claim 1, which is 2-chloro-5-thiazole sulfonato (trans-1,2-diaminocyclohexane) platinum.

18. A compound according to claim 1, which is 2-benzothiophene sulfonato (trans-1,2-diaminocyclohexane) platinum.

19. A compound according to claim 1, which is 6-methyl-2-benzothiophene sulfonato (trans-1,2-diaminocyclohexane) platinum.

20. A compound according to claim 1, which is 6-bromo-2-benzothiophene sulfonato (trans-1,2-diaminocyclohexane) platinum.

21. A compound according to claim 1, which is 6-chloro-2-benzothiophene sulfonato (trans-1,2-diaminocyclohexane) platinum.

22. A compound having the formula

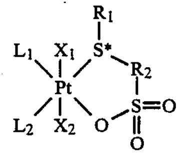

wherein $L_1$ and $L_2$ are individually ammonia or monodentate amine ligands or $L_1$ and $L_2$ together comprise a bidentate amine ligand;

$X_1$ and $X_2$ are two like groups selected from hydroxyl, chloride and bromide;

S* is sulfur; and $R_1$ and $R_2$ together with S* comprise a heterocyclic moiety selected from the group consisting of thiophene, thiazole, benzothiazole and benzothiophene, substituted or unsubstituted.

23. A compound according to claim 22, wherein $L_1$ and $L_2$ together comprise a bidentate amine ligand.

24. A compound according to claim 22, wherein said ligand is 1,2 diaminocyclohexane.

25. A method for prepating a coordinating complex of platinum comprising the steps of:

reacting a platinum salt with mono- or difunctional amine at a molar ratio of amine functionality to platinum of about 2:1 to yield a platinum-diamine complex;

obtaining a heterocyclic sulfur compound wherein a ring carbon atom adjacent to the heterocyclic sulfur atom has a pendant sulfonic acid moiety bonded thereto; and reacting said heterocyclic sulfur compound with said platinum amine complex to yield a product in which platinum is coordinated to two amine moieties, said heterocyclic sulfur atom, and said sulfonic acid group.

26. A method for making a coordination complex of platinum according to claim 25, further comprising the step of:

reacting said product with an oxidizing agent to yield a compound in which platinum has an oxidation state of +4 and is further coordinated to two hydroxy or halide groups.

27. A method according to claim 25, wherein said oxidizing agent is hydrogen peroxide, halogen, or a halogen acid.

28. A method according to claim 25 or 26, wherein the heterocyclic sulfur compound is substituted or unsubstituted thiophene.

29. A method according to claim 25 or 26, wherein the heterocyclic sulfur compound is substituted or unsubstituted thiazole.

30. A method according to claim 25 or 26, wherein the heterocyclic sulfur compound is substituted or unsubstituted benzothiophene.

31. A pharmaceutical preparation, comprising the compound of claim 1 in combination with a pharmaceutically-acceptable carrier.

32. A preparation according to claim 31, wherein the amino ligand of said compound is bidentate.

* * * * *